United States Patent [19]

Lee

[11] Patent Number: 4,863,457
[45] Date of Patent: Sep. 5, 1989

[54] DRUG DELIVERY DEVICE

[76] Inventor: David A. Lee, 827 Levering Ave., #807, Los Angeles, Calif. 90024

[21] Appl. No.: 186,700

[22] Filed: Apr. 22, 1988

Related U.S. Application Data

[63] Continuation of Ser. No. 934,096, Nov. 24, 1986, abandoned.

[51] Int. Cl.[4] .................... A61K 9/22; A61M 31/00; A61M 29/00; A61M 35/00
[52] U.S. Cl. .................... 604/891.1; 604/49; 604/104; 604/294; 424/428
[58] Field of Search .................. 604/893–894, 604/289, 294, 298, 300, 175, 8, 49, 265, 174, 175, 104–106, 265; 424/427–429; 623/4, 5; 128/334 R

[56] References Cited

U.S. PATENT DOCUMENTS

| | | | |
|---|---|---|---|
| 2,127,903 | 8/1938 | Bowen | 128/334 R |
| 2,593,980 | 4/1952 | Calicchio | 604/265 |
| 3,159,161 | 12/1964 | Ness | 604/175 |
| 3,620,218 | 11/1971 | Schmitt et al. | 128/334 R |
| 3,896,804 | 7/1975 | Ekbladh et al. | 604/174 |
| 4,037,604 | 7/1977 | Newkirk | 604/9 |
| 4,402,681 | 9/1983 | Haas et al. | 604/175 |
| 4,645,493 | 2/1987 | Ferrando et al. | 604/174 |
| 4,650,488 | 3/1987 | Bays et al. | 604/265 |
| 4,710,195 | 12/1987 | Giovinazzo | 623/6 |

FOREIGN PATENT DOCUMENTS 1210821  2/1986  U.S.S.R. ................ 604/297

Primary Examiner—C. Fred Rosenbaum
Assistant Examiner—Sharon Rose
Attorney, Agent, or Firm—Samuels, Gauthier, Stevens & Kehoe

[57] ABSTRACT

This invention relates to a medical device and a method of using the device to deliver a continuous controlled supply of a medication to a specific internal site. Specifically, the invention comprises an inert, biodegradable implant impregnated with one or more therapeutic agents designed to provide a controlled, localized and sustained release of the therapeutic agents. In a preferred embodiment, the device comprises an ocular implant which bioerodes within the eye environment thereby gradually releasing the therapeutic agents at the site to be treated until the entire implant eventually erodes without the need for further surgery. The invention is especially suitable for treating post-operative glaucoma patients.

17 Claims, 1 Drawing Sheet

DRUG DELIVERY DEVICE

This is a continuation of co-pending application Ser. No. 934,096 filed on Nov. 24, 1986, now abandoned.

BACKGROUND OF THE INVENTION AND DISCUSSION OF PRIOR ART

Although this invention has a variety of both optical and non-optical applications as described below, it is especially suitable for treating post-operative glaucoma patients. Because the use of this invention in treating post-operative glaucoma patients is representative of the other possible applications of this invention, this preferred embodiment will be described below in greater detail.

Glaucoma is a major cause of irreversible blindness in the United States. The National Advisory Eye Council estimated in 1978 that 62,000 Americans were blind as the result of glaucoma. Glaucomatous visual loss is usually associated with elevated intraocular pressures which damage the optic nerve. Glaucoma treatment is therefore directed toward lowering the intraocular pressure. In most glaucoma patients medical therapy (topical eye drops and oral tablets) adequately lowers intraocular pressure. When these measures are inadequate, laser therapy is often performed. If laser therapy is also unsuccessful, glaucoma surgery is required. Glaucoma filtration surgery is the most common type of glaucoma surgery. The purpose of this type of operation is to make an opening between the anterior chamber of the eye and the subconjunctival space to allow for the drainage of aqueous humor from the eye. This results in lowering the intraocular pressure. Failure of filtration surgery is usually attributed to the proliferation of fibroblasts and scarring at the filtering site. As a consequence of this scarring, the drainage canal opened by surgery is gradually obstructed by scar tissue and eventually sealed thereby necessitating further surgery.

Eyes undergoing glaucoma filtration surgery have a seventy-five percent to ninety percent chance of achieving intraocular pressure control following a first filtering procedure. The success rate of filtering surgery in eyes that have had unsuccessful previous filtering surgery is generally less than after the initial filtering procedure. Aphakic patients who undergo filtering surgery are also less likely to achieve adequate intraocular pressure control than phakic patients. The surgical prognosis for filtration operations are also less favorable for neovascular glaucoma and in young patients.

Various techniques have been tried to improve the success rate of glaucoma filtration surgery. These include the application of a variety of drugs that inhibit or prevent scarring and fibroblastic proliferation at the drainage site such as steroids and antimetabolites such as 5-fluorouracil. Artificial drainage implants of different designs have also been used in an attempt to form a permanent drainage tract into the extraocular tissues. For example, U.S. Pat. Nos. 3,788,327 (Donowitz et al.) and 4,402,681 (Haas et al.) disclose non-erodible ocular implants which consist of a body portion and a stem/-valve portion designed for the purpose of maintaining an open, drainage canal following glaucoma surgery to relieve intraocular pressure.

All of these prior art methods and devices, however, have their own particular limitations and complications. For drug treatment, there is the difficulty of regularly or continuously administering a controlled dose of the drug to a localized site over a prolonged period of time. The use of a non-erodible ocular implant may require subsequent surgery to remove the device. Often, scar tissue can proliferate and occlude the nonerodible ocular implant. The nonerodible ocular implant composed of a substance foreign to the body may be extruded over time or become a site of infection or inflammation.

One recent approach to these problems has involved the use of bioerodible polymer/drug combinations in a variety of ways to achieve a controlled regular or continuous administration of the drug. Bioerodible polymers are useful as carriers for many different types of drugs because they serve as a temporary matrix to hold the drug, but do not chemically interact with the drug. As the matrix erodes, the drugs are released and can diffuse into the tissues.

In one embodiment, the bioerodible polymer matrix is homogeneously impregnated with the drug so that the drug is released more or less continuously and uniformly as the supporting polymer matrix erodes. In another variation of this basic idea, a single reservoir of the drug in liquid or solution form is encapsulated by a semi-porous polymer matrix. The drug diffuses continuously out of the reservoir, through the polymer, and finally to the intended delivery area. In still a further variation, tiny discrete "pockets" of the drug are encapsulated throughout the polymer. If the polymer is bioerodible, eventually it will completely dissolve thereby releasing all of the impregnated or encapsulated drug.

For example, U.S. Pat. Nos. 3,993,071 (Higuchi et al.); 3,986,510 (Higuchi et al.); 3,981,303 (Higuchi et al.); and, 3,960,150 (Hussain et al.) broadly disclose the concept of bioerodible ocular inserts designed for continuous, controlled administration of a medication to the eye. These patents comprehensively disclose a wide array of the following features:

(a) ocular problems which can benefit from the use of the subject inserts, specifically including treatment of glaucoma;

(b) useful drug/bioerodible matrix combinations, specifically including the group of miotics and anticholinesterases such as pilocarpine;

(c) useful insert shapes including ellipsoid, donut-shape, bean-shape, banana-shape, circular, and rectangular; and, (d) drug release control techniques ranging from a more or less homogeneous bioerodible matrix with medication dispersed throughout to a single drug reservoir inside the support matrix including one embodiment employing microencapsulation of the drug within the support matrix.

Other recent patents which disclose various types and shapes of bioerodible ocular inserts include U.S. Pat. Nos. 3,995,635 (Higuchi et al.) 4,142,526 (Zaffroni et al.); 3,963,025 (Whitaker et al.); 4,484,922 (Rosenwald); 4,439,198 (Brightman); 3,811,444 (Heller et al.); 3,867,519 (Michaels); and 3,962,414 (Michaels).

U.S. Pat. Nos. 4,190,642 (Gale et al.); 4,179,497 (Cohen et al.); and 3,911,098 (Capozza) show various drug/matrix combinations especially intended for treating eye problems. Gale et al. discloses a non-erodible ocular insert intended specifically for managing intraocular pressure, and Cohen et al. discloses an erodible insert for the same purpose. All of the above-cited prior art is hereby specifically incorporated herein by reference.

As is evident from a review of the above patents, the area of bioerodible eye inserts which serve as controlled-rate drug delivery vehicles is a very crowded field. None of the above-cited patents, however, discloses a bioerodible ocular implant capable of controlled-rate drug delivery to a specific localized intraocular site nor one which is designed to function so as to maintain a drainage canal utilizing both therapeutic and mechanical means. As used in this application, the term "implant" is intended to specifically distinguish the bioerodible devices of this invention, which are designed for internal surgical placement, from the "inserts" of the prior art which are employed externally or in areas accessible without surgery such as at the surface of the conjunctival membrane in the eye.

All of the bioerodible inserts disclosed by the prior art are designed and specifically intended for extraocular use. They are typically positioned on the surface of the conjunctival membrane between the upper or lower lids of the eye and the sclera or outer surface of the eyeball (e.g. FIGS. 1 and 2, described at col. 5, ll. 11–44, of U.S. Pat. No. 3,993,071). As a result, as the polymer matrix erodes, medication is delivered to the entire conjunctival area and across the entire surface of the cornea. Such generalized delivery of the medication may restrict the type or concentration of medication that can be employed. Furthermore, because the inserts of these prior art patents are applied to the surface of the eyeball, at best only a small fraction of the medication can reach intraocular sites where the medication may really be needed. Even to the extent that some of the medication may penetrate to intraocular sites, the devices and methods of the prior art patents in this area serve only as vehicles for holding and gradually releasing the medication. The structural elements of these devices serve no beneficial mechanical functions.

OBJECTS OF THE INVENTION

A principal object of this invention is to provide an inert, bioerodible implant fully or partially impregnated with one or more therapeutic agents designed to provide a controlled, localized and sustained release of the therapeutic agents.

A further object is to provide a bioerodible implant designed to be internally implanted so as to deliver medication to a specific, localized site.

Still a further object is to provide a bioerodible implant and a method for using it such that the physical shape and structure of the supporting polymer matrix serve a beneficial mechanical function as well as serving as a vehicle for the medication.

These and other objects and advantages of this invention will become apparent in the following description.

DETAILED DESCRIPTION AND PREFERRED EMBODIMENTS

Figure 1:
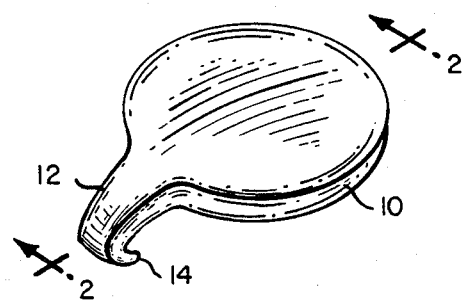
FIG. 1 is a schematic perspective view of one embodiment of the bioerodible implant of this invention especially designed for treating post-operative glaucoma patients.
Figure 2:
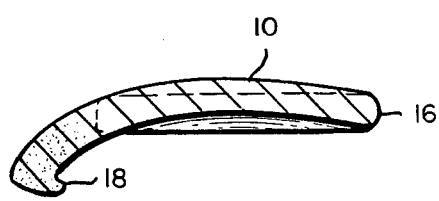
FIG. 2 is a sectional side view of the bioerodible implant along the axis 2—2 in FIG. 1.

Referring to FIG. 1, in the preferred embodiment the bioerodible implant of this invention comprises a more or less flat, circular base portion 10 and a tapered stem portion 12. The outer end of stem 12 may optionally be curved around to form a hook or anchor 14 to assist in retaining the implant in place. Stem 12 may be located in substantially the same plane as base 10 or it may be disposed at an angle ranging from about 0°–180° with respect to the plane of base 10. As shown in FIG. 4, stem 12 is disposed at an angle of about 30° with respect to the plane of base 10. Base 10 may be substantially flat, or it may be slightly convex depending on the intended use. As shown in FIGS. 1–4, where base 10 is going to be implanted adjacent to a convex surface such as the surface of an eyeball, it is desirable for base 10 to have a similar convexity to ensure a good fit. Although base 10 might be fashioned in any known shape, such as rectangular or triangular to accommodate special applications, in general a circular or oval shape will be preferred because the smooth, rounded edge avoids possible tissue damage which could result from sharp corners. Similarly, as better seen in FIG. 2, the outer edge 16 of base 10 and tip 18 of stem 12 are also rounded for the same reasons.

Base 10 and stem 12 can be fashioned as a single unit or as separate elements from any of the numerous suitable bioerodible polymers which are recognized in the art. Such polymer matrices include, but are not limited to, the polyanhydrides such as poly[bis (p-carboxyphenoxy) propane anhydride], poly (terephthalic acid anhydride), and their copolymers with sebacic acid; poly-3-hydroxybutyrate, polyglycolic acid, poly DL lactic acid, poly L lactic acid, and poly (glycolide-co-L-lactide). The implant can be composed of one or a mixture of several different polymers in a combination which is most suitable for its purpose. For some applications, it will be desirable to fabricate the base and the stem from different polymers, and such variations are within the scope of this invention. Because the implants of this invention are intended for internal applications, the polymer matrices should consist of biologically inert substances (non-cytotoxic, non-inflammatory, non-mutagenic, and non-teratogenic) which, when impregnated with drugs that prevent fibroblastic proliferation and scarring, would provide a controlled, localized, and sustained release of the drug over an extended period of time and then would eventually disappear leaving an open fistula.

A variety of drugs may be usefully incorporated into the implants of this invention such as 5-fluorouracil, bleomycin, daunomycin, heparin, cortisone, triamcinolone, betaaminopropionitrile, colchicine, urokinase, and others to prevent the closure of the subject site. These drugs may be used in a variety of amounts and combinations to optimize the success of the filtering operation. Specific optimum combinations of polymers and drugs, as well as optimum drug dosages, are either disclosed in the prior art or, in a particular case, can be readily determined through routine experimentation.

Stem 12 is designed such that when base 10 is properly positioned stem 12 protrudes into a canal, passageway, orifice or other internal cavity which is meant to be kept open. In this manner, stem 12 serves not merely as a vehicle for delivering medication to a specific internal site but, in addition, the structural elements of stem 12 serve as mechanical supports to prevent or retard closure of the passageway or cavity by scarring or fibroblastic proliferation. In other embodiments of this invention, a different shape or structure of the implant may be used to accommodate a different mechanical function in addition to its drug delivery function. In one embodiment of this invention, both the base 10 and stem 12 of the implant can be impregnated with the therapeutic agent. In the preferred embodiment, however, in order to localize the area to which the medication is delivered, only stem 12 contains the therapeutic agent. In another variation also within the scope of this invention instead of impregnating stem 12 of the implant with the therapeutic agent, microencapsulation techniques as disclosed in the prior art can be used to create tiny discrete reservoirs or pockets of the medication throughout the stem. The medication will be released to the desired area as the supporting polymer matrix gradually erodes in situ.

Figure 3:
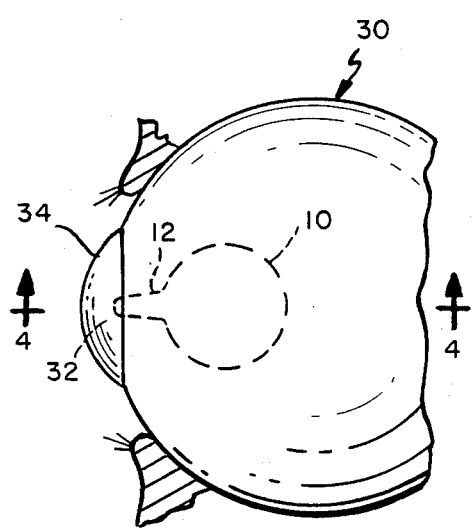
FIG. 3 is a schematic top view of an eyeball which is being treated with the bioerodible implant of this invention.
Figure 4:
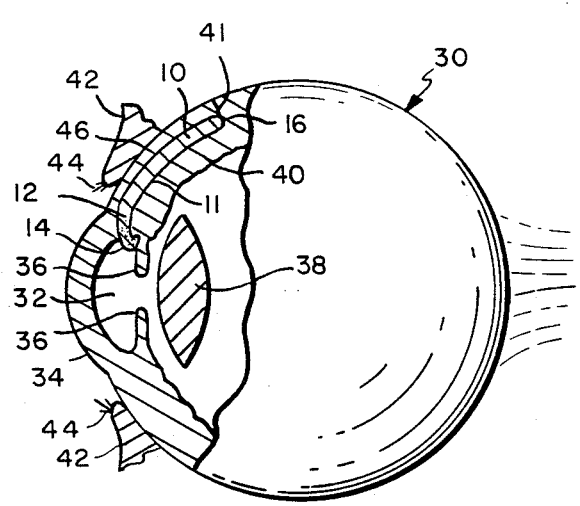
FIG. 4 is a sectional side view of the eyeball along the axis 4—4 in FIG. 3.

FIGS. 3 and 4 illustrate the preferred embodiment of this invention wherein the bioerodible implant is utilized to treat post-operative glaucoma. FIG. 3 is a schematic top view of an eyeball 30 which is being treated with a bioerodible implant comprising base 10 and tapered stem 12 as described above. The implant is positioned either in the subconjunctival space between the conjunctival membrane overlying it and the sclera beneath it or within the sclera itself, being covered by a partial-thickness scleral flap. Alternatively, the implant of this invention may be positioned in a cyclodialysis cleft between the ciliary body and the sclera. The base 10 is connected to the stem 12 which protrudes into the anterior chamber 32 located behind the cornea 34.

FIG. 4 is a sectional side view of the eyeball 30 along the axis 4—4 in FIG. 3. FIG. 4 more clearly shows the interior and exterior features of the eyeball including the anterior chamber 32 located behind cornea 34, the iris 36, the lens 38, and eyelids 42 together with lashes 44. In FIG. 4, it can be clearly seen how the bioerodible implant of this invention is positioned in the sclera 40 below the conjunctival membrane 46 located beneath eyelids 42. The partial-thickness scleral flap, as described above, is defined by the outer edge of base 10, the conjunctival membrane 46 and incision or slit 41 through which the device is implanted in the sclera 40. As described above, stem 12 extends from base 10 into anterior chamber 32. Anchor tip 14 at the end of stem 12 helps to secure the implant firmly in place. The positioning of base 10 and stem 12 ensures that communication is maintained between anterior chamber 32 and Schlemm's canal (not shown) at the base of the cornea 34 as well as between the anterior chamber and the subconjunctival region beneath conjunctival membrane 46 thereby ensuring continued drainage of aqueous humor and preventing a recurrence of the pressure buildup which caused the glaucoma. Stem 12, as it erodes in situ, slowly releases medication to retard the formation of scar tissue and keep the passageway open between anterior chamber 32 and Schlemm's canal as well as between the anterior chamber and the subconjunctival region. At the same time, the structural features and rounded, tapered shape of stem 12 serve a mechanical function in keeping the passageway from scarring over.

Polymers implanted subconjunctivally may be useful in releasing a variety of drugs commonly used to treat glaucoma, for example timolol, epinephrine, pilocarpine, and carbonic anhydrase inhibitors. The bioerodible implants of this invention are especially valuable in situations of poor patient compliance or poor drug penetration into ocular tissues. The localized release of drugs from biodegradable polymers lessens the change of adverse systemic reactions and increases the efficiency of drug delivery. An added advantage of using solid bioerodible polymers as drug carriers is that they can be removed, together with the medication, if any adverse drug side effects or toxicity occur. This is not possible with subconjunctivally injected drugs. The shapes and sizes of the implants containing drugs can be variable and "tailor-made" depending on their purpose, anatomical location, and desired duration of action.

For this preferred embodiment of the invention, the base 10 can be fashioned in a variety of shapes and sizes, but ideally it would be in a round or ovoid shape approximately five millimeters in diameter and one millimeter in thickness.

The underside 11 of base 10 can be flat or can be shaped to conform to the sclera with a radius of curvature of approximately twelve millimeters. The edges 16 of base 10 should be smooth to avoid trauma or irritation to adjacent tissues. Base 10 may have a single or multiple perforations to increase its surface area and vary its degradation rate as well as for the purpose of fixation to the sclera with a suture or several sutures. The size and shape of base 10 should be able to be altered prior to its implantation at the time of surgery.

Stem 12 as used in this preferred embodiment is approximately two millimeters long and one millimeter wide. Its composition of polymer and drug can be the same as or different from that of base 10. Stem 12 extends from the limbus of the eye into the anterior chamber 32 and should not be in contact with the corneal endothelium or the lens 38 at anytime. Stem 12 can be of various shapes: a solid cylinder, a hollow tube, or a groove on the side of the cylinder. The end of stem 12 may have a hook 14 to anchor it to the sclera of the eye and to stabilize and fixate its position. Stem 12 should extend from the plane of base 10 at approximately a forty-five degree angle. The edges of stem 12 should be smooth to avoid or minimize trauma to adjacent tissues. Stem 12 should be able to be detached or adjusted prior to its implantation.

The bioerodible implants of this invention are by no means limited to treatment of post-operative glaucoma patients. A wide variety of ocular and other conditions may benefit from the use of the bioerodible implants. Among these are inflammation, infection, scarring, and post-operative situations that require prolonged and sustained drug treatment over extended periods of time. In many situations patients are unable to or have great difficulty in taking their eye medications, especially eyedrops in elderly people or very young people. In these situations, a depot of drug placed in the location of interest that will be released over variable periods of time may be useful.

Extra and intraocular inflammation treatment may benefit from polymers impregnated with corticosteroids, cyclosporin, or prostaglandin inhibitors at the site of inflammation. Extra and intraocular infections may be treated by polymers containing various antibacterial, antiviral, antifungal, and antiparasitic agents placed close to the site of infection. In certain post-operative situations, such as after cataract surgery, steroids and antibiotics can be deposited in a polymer matrix at the site of surgery to prevent inflammation and infection. In other post-operative situations, prevention of scarring or enhancement of wound healing are desired; and, drugs that would be useful here can be delivered via the bioerodible implants of this invention.

The following examples illustrate other possible applications for the bioerodible implants of this invention:

EXAMPLE #1

A disc-shaped implant containing antibiotics and steroids may be placed subconjunctivally near the wound at the conclusion of cataract surgery to deliver medication (antibiotic, steroids, or agents that enhance wound healing, etc.) over several weeks post-operatively. If problems occur with elevated intraocular pressure secondary to the steroids, the entire polymer can be easily removed under topical anesthesia.

EXAMPLE #2

At the conclusion of surgery for the repair of retinal detachment, medicated polymers (steroids and antibiotics, etc.) can be placed at the site of the scleral buckle to decrease the risk of infection or inflammation post-operatively. The scleral buckle may also be composed of the bioerodible material impregnated with medication.

EXAMPLE #3

Polymers impregnated with antibiotic, anti-inflammatory, anti-neovascular, and anti-fibroblastic drugs may be implanted in the vitreal cavity of the eye at the conclusion of intraocular vitreo-retinal surgery to prevent infection, inflammation, neovascularization, and scarring in the retina and vitreal cavity. This would be especially useful in cases of endophthalmitis, severe veitis, proliferative diabetic retinopathy, and proliferative vitreo-retinopathy.

EXAMPLE #4

Polymers impregnated with anti-scarring drugs can be used in strabismus surgery in situations where multiple extraocular muscle procedures have been performed or in diseases which cause fibrosis of the extraocular muscles such as Grave's ophthalmopathy or previous orbital trauma. The medicated polymers could be implanted at the desired location intraoperatively when the old scar tissue has been removed and/or the extraocular muscles have been readjusted.

Many other variations and modifications of my basic design will be readily apparent to those skilled in the art. All such variations and modifications are within the spirit and the scope of this invention and, therefore, are intended to be encompassed by the following claims:

Having described my invention, what I claim is:

1. A method for maintaining an open internal passageway comprising surgically implanting a bioerodible drug delivery device at an internal orifice, said device comprising a base and a stem, said stem being shaped so as to substantially fill said orifice, said base and stem consisting essentially of a biologically inert bioerodible polymer matrix and, incorporated therein, a compatible therapeutic agent selected from one or more drugs, at least one of which drugs inhibits scarring and fibroblastic proliferation, and positioning said device such that at least a portion of said stem extends into said orifice.

2. A method for controlled, localized and sustained delivery of a therapeutic agent to an internal orifice and for inhibiting scarring and closure of surgically-created drainage canal at said orifice comprising the following steps:

(a) preparing a bioerodible implant apparatus comprising a base and a stem consisting essentially of a biologically inert bioerodible polymer matrix having incorporated therein a therapeutic agent selected from one or more drugs, at least one of which drugs inhibits scarring and fibroblastic proliferation;

(b) shaping said stem so as to substantially fill said orifice;

(c) surgically implanting said implant at said orifice; and, (d) positioning said base such that at least a portion of said stem protrudes into said drainage canal and is in contact with at least a portion of the inner surface of said canal whereby said drainage canal is maintained utilizing both therapeutic and mechanical means.

3. The method of claim 2 wherein the polymer matrix comprising said stem is impregnated with said therapeutic agent during the preparation step.

4. The method of claim 2 wherein the preparation step includes the further step of shaping the stem so as to provide a hook at the end of said stem in order to anchor the implant in place when the stem is positioned into said internal orifice.

5. A bioerodible drug delivery device for surgical intraocular implantation at a subconjunctival orifice comprising a base and a stem each consisting essentially of a bioerodible polymer matrix and, incorporated therein, a compatible therapeutic agent selected from one or more drugs, at least one of which drugs inhibits scarring and fibroblastic proliferation, wherein said base is of a generally flat shape with rounded edges and said stem is rounded and tapered so as to mate with said subconjunctival orifice whereby a drainage canal is maintained utilizing both therapeutic and mechanical means.

6. The drug delivery device of claim 5 wherein the end of said stem curves around to form a hook.

7. The drug delivery device of claim 5 wherein only said stem contains said therapeutic agent.

8. The drug delivery device of claim 7 wherein the polymer matrix comprising the stem is impregnated with said therapeutic agent.

9. The drug delivery device of claim 7 wherein said therapeutic agent is incorporated in said polymer matrix in microencapsulation form.

10. A method for maintaining an open subconjuctival orifice comprising surgically implanting the drug delivery device of claim 5 and positioning said base such that at least a portion of said stem extends into said orifice.

11. The method of claim 10 wherein the preparation step includes the further step of shaping the stem so as to provide a hook at the end of said stem in order to anchor the implant in place when the stem is positioned protruding into said internal cavity.

12. A bioerodible intraocular implant apparatus for treating post-operative glaucoma patients by implantation at the site of a surgically-created drainage canal comprising a generally flat, circular base and a tapered stem consisting essentially of a bioerodible polymer matrix having incorporated therein a therapeutic agent for preventing fibroblastic proliferation and scarring wherein said tapered stem is of a shape and dimensions so as to mate with said drainage canal whereby said drainage canal is maintained utilizing both therapeutic and mechanical means.

13. A method for treating post-operative glaucoma patients comprising surgically implanting the bioerodible implant of claim 12 within the sclera or subconjunctival region such that said tapered stem extends into the surgically-created drainage canal between the anterior chamber and the subconjunctival region.

14. A method for maintaining an open internal passageway comprising surgically implanting a bioerodible drug delivery device at a subconjunctival orifice, said device comprising a base and a stem each consisting essentially of a bioerodible polymer matrix and, incorporated therein, a compatible therapeutic agent selected from one or more drugs, at least one of which drugs inhibit scarring and fibroblastic proliferation, and positioning said device such that at least a portion of said stem extends into said orifice.

15. A method for controlled, localized and sustained delivery of a therapeutic agent to a subconjunctival orifice and for inhibiting scarring and closure of a surgically-created drainage canal at said orifice comprising the following steps:
 (a) preparing a bioerodible implant apparatus comprising a base and a step each consisting essentially of a bioerodible polymer matrix having incorporated therein a therapeutic agent selected from one or more drugs, at least one of which drugs inhibits scarring and fibroblastic proliferation, wherein said base is of a generally flat shape with rounded edges and said stem is generally rounded and tapered;
 (b) shaping said stem so as to mate with said subconjunctival orifice;
 (c) surgically implanting said implant at said subconjunctival orifice; and,
 (d) positioning said base such that at least a portion of said stem protrudes into said drainage canal and is in contact with at least a portion of the inner surface of said canal whereby said drainage canal is maintained utilizing both therapeutic and mechanical means.

16. The method of claim 15 wherein the polymer matrix comprising said stem is impregnated with said therapeutic agent during the preparation step.

17. The method of claim 15 wherein the preparation step includes the further step of shaping the stem so as to provide a hook at the end of said stem in order to anchor the implant in place when the stem is positioned protruding into said orifice.

* * * * *

UNITED STATES PATENT AND TRADEMARK OFFICE
CERTIFICATE OF CORRECTION

PATENT NO. : 4,863,457
DATED : September 5, 1989
INVENTOR(S) : David A. Lee

It is certified that error appears in the above—identified patent and that said Letters Patent is hereby corrected as shown below:

Col. 8, line 24 - after "positioned" insert the word

-- protruding --.

Col. 9, line 14 - delete "inhibit" and insert therefor

-- inhibits --.

Signed and Sealed this

Twenty-seventh Day of April, 1993

Attest:

MICHAEL K. KIRK

Attesting Officer          Acting Commissioner of Patents and Trademarks